United States Patent
Webb et al.

[11] Patent Number: 5,830,226
[45] Date of Patent: Nov. 3, 1998

[54] MICROSURGICAL SCALPEL ASSEMBLY

[75] Inventors: Nicholas J. Webb, Wrightwood, Calif.; Richard W. Mendius, Millington, Tenn.

[73] Assignee: Eagle Vision, Inc., Memphis, Tenn.

[21] Appl. No.: 850,867

[22] Filed: May 2, 1997

Related U.S. Application Data

[63] Continuation of Ser. No. 702,850, Aug. 26, 1993, abandoned, which is a continuation of Ser. No. 379,857, Jan. 26, 1995, abandoned, which is a continuation of Ser. No. 054,174, Apr. 30, 1993, abandoned.

[51] Int. Cl.⁶ .................................................. A61B 17/32
[52] U.S. Cl. ................................................................ 606/167
[58] Field of Search ................................. 606/167, 166, 606/172, 181; 30/286, 295, 162

[56] References Cited

U.S. PATENT DOCUMENTS

| | | |
|---|---|---|
| 739,371 | 9/1903 | Allen . |
| 1,735,271 | 11/1929 | Groff . |
| 3,706,106 | 12/1972 | Leopoldi . |
| 3,793,726 | 2/1974 | Schrank . |
| 3,906,626 | 9/1975 | Rivli ............................................ 30/162 |
| 4,071,952 | 2/1978 | Meshulam et al. . |
| 4,165,745 | 8/1979 | Heifetz ...................................... 606/174 |
| 4,499,898 | 2/1985 | Knepshield et al. ...................... 606/167 |
| 4,552,146 | 11/1985 | Jensen et al. ........................... 606/172 X |
| 4,576,164 | 3/1986 | Richeson . |
| 4,635,914 | 1/1987 | Kabanek . |
| 4,674,500 | 6/1987 | De Satnick ................................. 30/286 |
| 4,719,915 | 1/1988 | Porat et al. . |
| 4,733,662 | 3/1988 | De Satnick et al. .................... 30/162 X |
| 4,735,202 | 4/1988 | Williams ................................. 30/295 X |
| 4,759,363 | 7/1988 | Jensen ...................................... 606/172 |
| 4,825,545 | 5/1989 | Chase et al. . |
| 4,903,390 | 2/1990 | Vidal et al. . |
| 5,026,386 | 6/1991 | Michelson . |
| 5,059,210 | 10/1991 | Clark et al. . |
| 5,092,852 | 3/1992 | Poling . |
| 5,222,951 | 6/1993 | Abidin et al. ........................... 30/162 X |
| 5,292,329 | 3/1994 | Werner ..................................... 606/167 |

FOREIGN PATENT DOCUMENTS

| | | |
|---|---|---|
| 8703525 | 10/1987 | Germany . |
| 3722899 | 1/1989 | Germany . |
| 490072 | 1/1970 | Switzerland . |

OTHER PUBLICATIONS

Mueller "The Surigcal Armamentarium" (1980) p. 3.

*Primary Examiner*—Michael H. Thaler
*Attorney, Agent, or Firm*—Vorys Sater Seymour & Pease LLP

[57] ABSTRACT

A microsurgical scalpel assembly including an elongate scalpel handle and a scalpel blade affixed at one end of the scalpel handle and a shield releasably affixed to the one end of the scalpel handle and extending away from the handle to operably surround the scalpel blade to isolate sharp surfaces of the scalpel blade from a surgeon and to protect the blade from damage during a re-sterilization autoclave procedure.

2 Claims, 5 Drawing Sheets

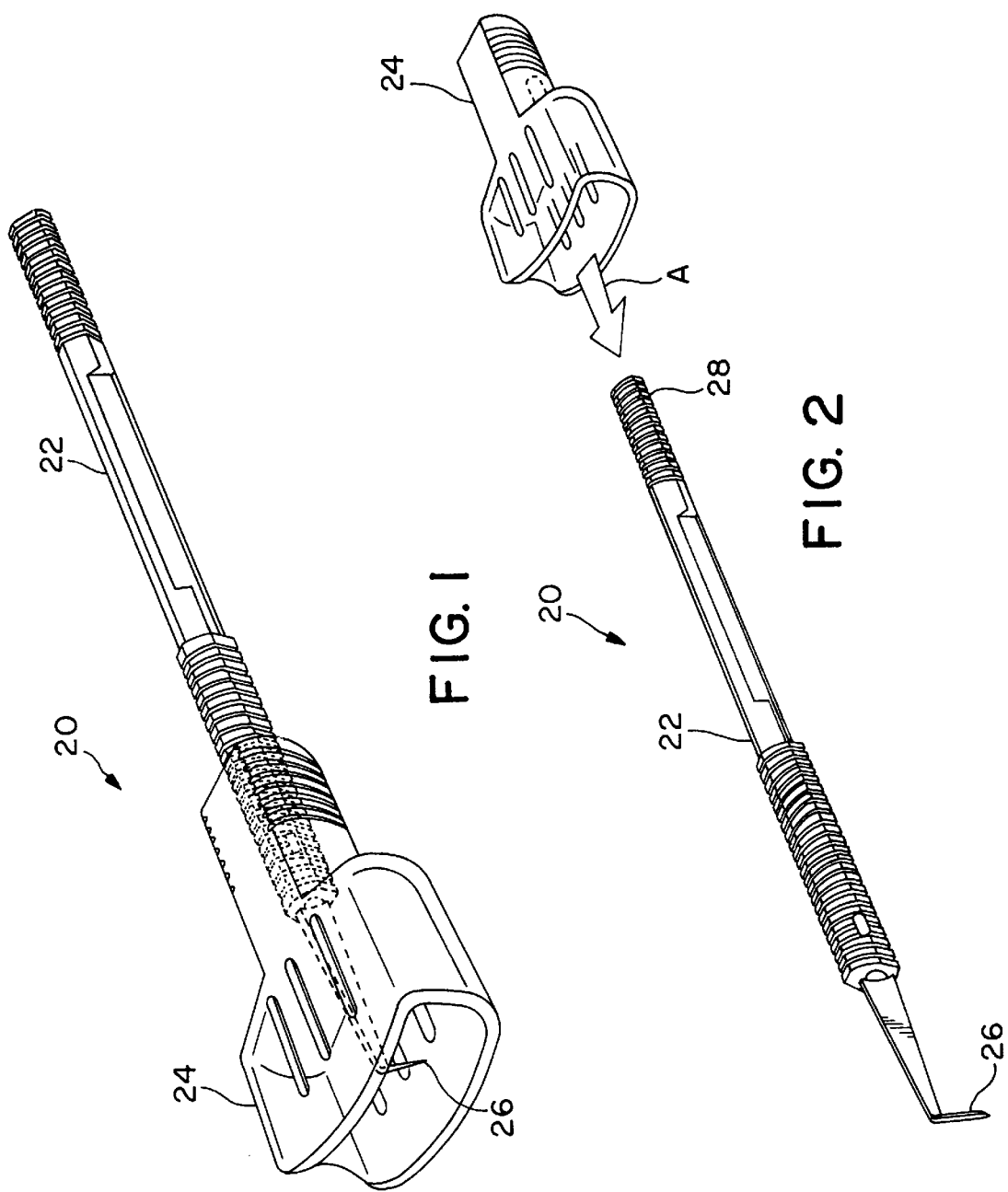

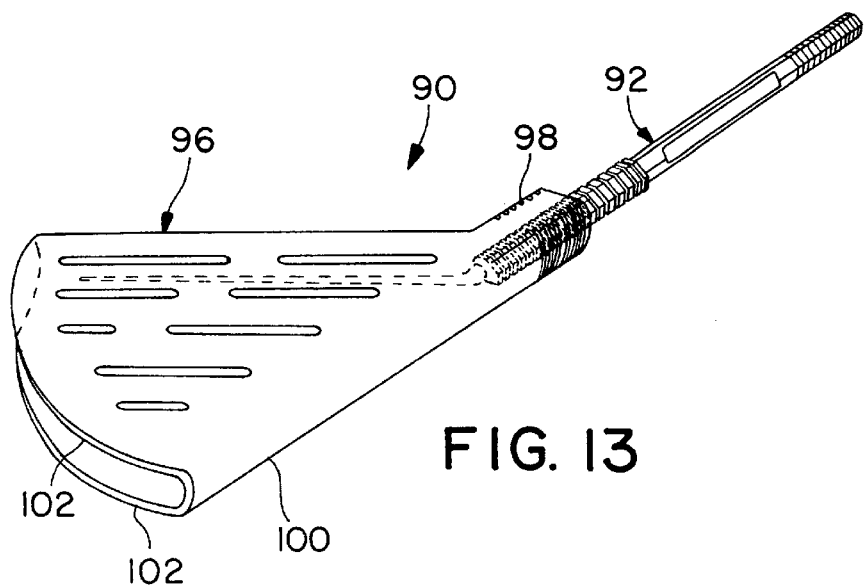
FIG. 13
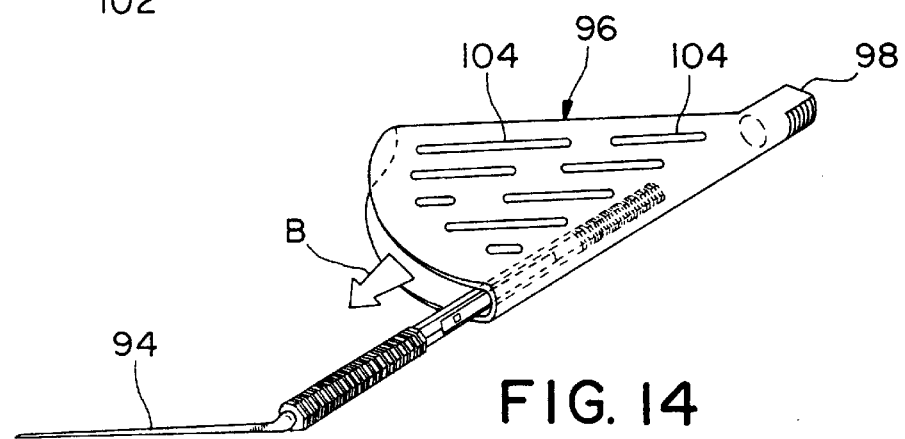
FIG. 14
FIG. 16
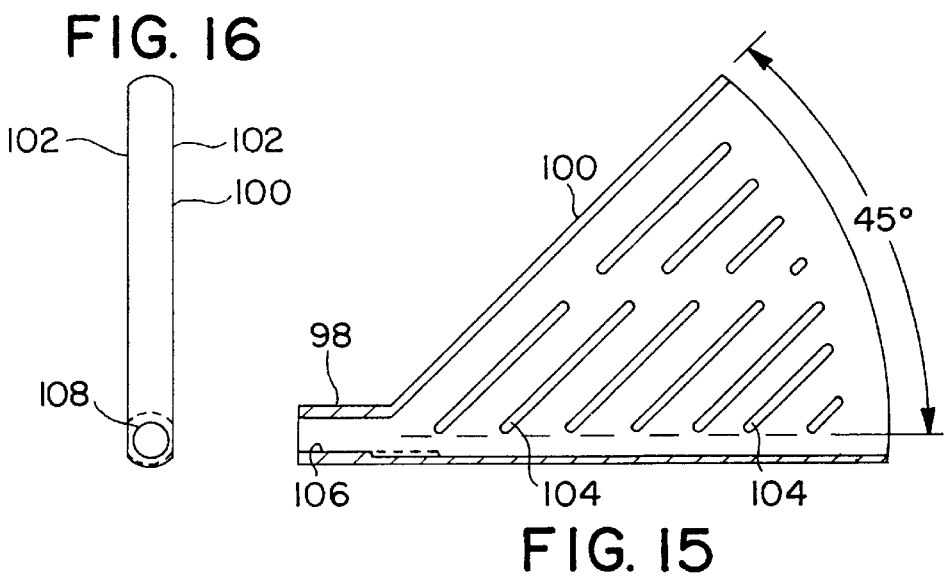
FIG. 15

MICROSURGICAL SCALPEL ASSEMBLY

This application is a continuation of application(s) Ser. No. 08/702,850 filed on Aug. 26, 1996, abandoned, which is a continuation of application Ser. No. 08/379,857 filed Jan. 26, 1995 abandoned, which is a continuation of application Ser. No. 08/054,174, filed Apr. 30, 1993, abandoned.

BACKGROUND OF THE INVENTION

This invention relates to a microsurgical scalpel assembly. More particularly this invention is directed to a microsurgical scalpel assembly with enhanced safety and useability characteristics for an operating surgeon and a concomitant capability of being economically utilized as a high precision instrument.

In the surgical scalpel industry and particularly the microsurgical scalpel arena at least two problems are becoming of increasing concern. One level of concern surrounds the economic utilization of surgical instruments in the medical community. In this connection, low cost scalpels have been envisioned which are essentially disposable, however, initial point sharpness and cutting edge quality is less than exists in more expensive, high precision instruments. However, with increasing economic pressures being placed upon the medical community, tradeoffs are being seriously evaluated and low cost disposable scalpels are being utilized as opposed to more high quality precision instruments.

In addition to instrument quality and an attendant potential for less than optimum surgical results the medical community has a growing concern with respect to body fluid transmitted diseases. In this, acquired immune deficiency syndrome (AIDS), Hepatitis B, etc., are becoming prevalent enough such that health care professionals are increasingly concerned about maintaining an uncompromising isolation integrity with respect to the body fluid of patients. Although wearing disposable rubber gloves is a precaution of preference, and even in certain instances wearing double gloves is an accepted practice, when utilizing a sharply pointed and/or sharp bladed surgical instrument such as microsurgical scalpels, puncture wounds, even though a double glove, is not only conceivable but almost inescapable. It has been estimated that as much as two percent of sharp product handling results in accidental stabs in the medical community.

The difficulty suggested in the proceeding are not intended to be exhaustive but rather are among many which may tend to limit the effectiveness of prior microsurgical scalpels. Other noteworthy problems may also exist; however, those presented above should be sufficient to demonstrate that microsurgical scalpels appearing in the past will admit to worthwhile improvement.

OBJECTS OF THE INVENTION

It is, therefore, a general object of the invention to provide a novel microsurgical scalpel assembly which will obviate or minimize problems of the type previously described.

It is a specific object of the invention to provide a microsurgical high quality scalpel which may be advantageously re-sterilized and reused in a microsurgical procedure.

It is a related object of the invention to provide a microsurgical scalpel assembly wherein sharp point and cutting edge integrity of high quality scalpels may be faciley maintained during and autoclaving re-sterilization procedures in the presence of other instruments.

It is another object of the invention to provide a microsurgical scalpel assembly wherein the tendency of a surgeon to receive a puncture wound during handling is minimized.

It is a further object of the invention to provide a microsurgical scalpel assembly wherein blade shapes and lengths of a large variety may be accommodated while concomitantly providing isolation integrity of the blade for a surgeon during handling and permitting re-sterilization without jeopardizing the sharpness integrity of the microsurgical scalpel,

BRIEF SUMMARY OF A PREFERRED EMBODIMENT OF THE INVENTION

A preferred embodiment of the invention which is intended to accomplish at least some of the foregoing objects includes an elongate scalpel handle and a scalpel blade affixed at one end of the scalpel handle and extending away from the handle. A shield is releasably affixed to the one end of the scalpel handle and extends away from the handle to operably surround the scalpel blade to isolate the blade from puncture contact with a surgeon during handling. The shield further operably isolates a tip and cutting edge of the microsurgical blade during an autoclaving operation wherein other instruments may be positioned in close physical proximity. Further, the shield is provided with a plurality of elongate apertures which are positioned adjacent the scalpel blade thus permit circulation and full sterilization during an autoclaving operation.

THE DRAWINGS

Other objects and advantages of the present invention will become apparent from the following detailed description of preferred embodiments taken in conjunction with the accompanying drawings wherein:

FIG. 1 is an axonometric view of a microsurgical scalpel assembly in accordance with a preferred embodiment of the invention.

FIG. 2 is an exploded axonometric view of a microsurgical scalpel assembly as depicted in FIG. 1 wherein a scalpel blade shield is disclosed in a position to be mounted about the scalpel blade by being slid from the base of the scalpel to and surrounding the blade end of the scalpel;

FIG. 13 is an axonometric view of a microsurgical scalpel assembly in accordance with still another preferred embodiment of the invention;

FIG. 14 is an exploded axonometric view of a microsurgical scalpel assembly as depicted in FIG. 13;

FIG. 15 is a plan view of a microsurgical shield in accordance with the embodiment of the invention depicted in FIGS. 13 and 14;

FIG. 16 is an end view of the microsurgical shield as depicted in FIG. 15;

Figure 3:
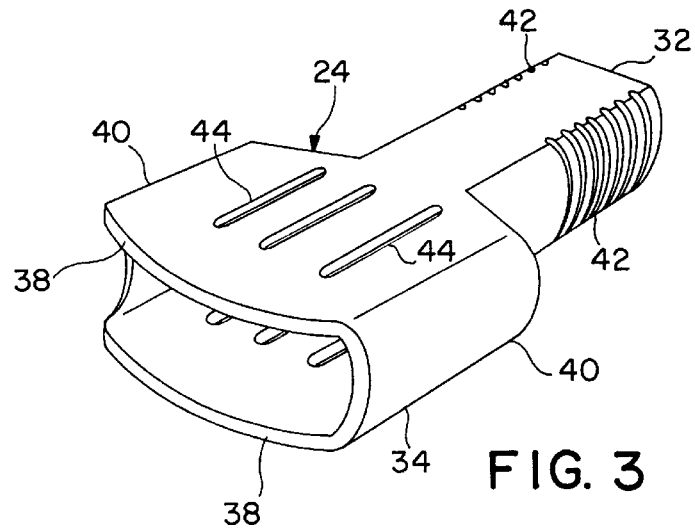
FIG. 3 is a axonometric detailed view of a scalpel blade shield in accordance with a preferred embodiment of the invention.

FIGS. 17 a–c disclose a sequence of views of a surgeon applying a microsurgical scalpel shield to a microsurgical scalpel in accordance with the subject invention; and FIGS. 18 a–c disclose a corresponding sequence of removing a microsurgical scalpel shield from a scalpel in accordance with the subject invention.

DETAILED DESCRIPTION

Illustrative Structural Embodiments

Turning to FIG. 1 there will be seen an axonometric scalpel assembly 20 in accordance with a preferred embodiment of the invention. In this, the assembly includes a generally elongate scalpel handle 22 and a scalpel shield 24 which is releasably affixed to one end of the scalpel handle. It will be noted that the shield extends away from the scalpel handle and is operable to isolate a scalpel blade 26 from contact by a physician during handling of the microsurgical scalpel assembly. The blade depicted is intended to be illustrative and other shaped blades such as arrow blades or phacoemulsification incisions and placement of intraocular lenses, radial keratotomy blades, crescent, circular and general dissection blades are all contemplated by the subject invention.

Turning now specifically to FIG. 2, it will be seen that the microsurgical scalpel assembly 20 is depicted in an expanded condition wherein the microsurgical shield 24 is directed toward a base end 28 of the scalpel handle 22 in the direction of arrow A. The shield 24, as will be discussed in detail presently hereafter, is designed to be slid from the base of the surgical instrument to the sharp blade end and thus avoid any likelihood or possibility that a surgeon will need to thread a sharp blade into a shield and thus create a possibility of a stab wound during an inattentive or hurried motion.

Figures 4, 6:
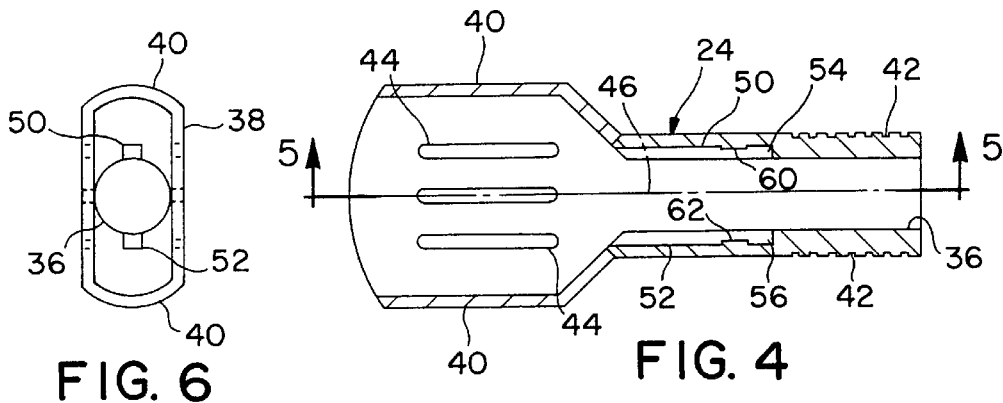
FIG. 4 is a cross-section view of the microsurgical scalpel shield depicted in FIG. 3.
FIG. 6 is an end view of the microsurgical scalpel shield depicted in FIG. 4.
Figures 5, 7:
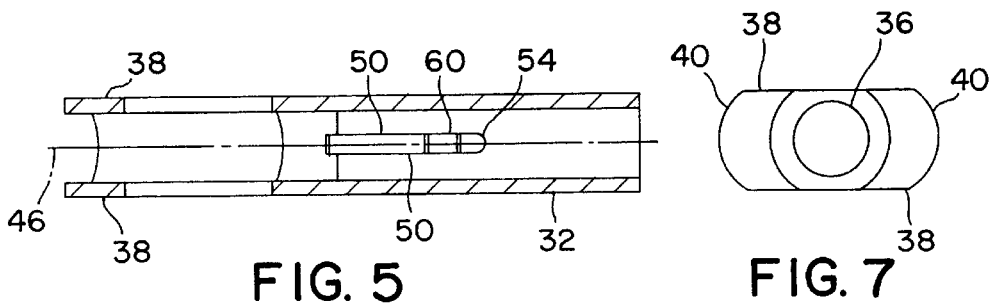
FIG. 5 is a cross-sectional view taken along section line 5—5 in FIG. 4.
FIG. 7 is an end view of the microsurgical scalpel shield depicted in FIG. 5.

Referring now to FIGS. 3–7 there will be seen various detailed views of a preferred embodiment of a microsurgical scalpel shield in accordance with the subject invention. The microsurgical shield includes a base portion 32 and a hood portion 34. The base portion comprises a generally elongate cylinder having an axial bore 36, note FIGS. 4, and 6–7, which is circular in cross section and coaxially extends through the generally cylindrical base member. The hood 34 is expanded outwardly from the base member and is generally or essentially rectangular in cross-sectional configuration, note FIG. 6. the hood 34 includes a pair of mutually opposing long sidewall surfaces 38 and short sidewall surfaces 40. The sidewalls 38 are generally planar in configuration while the shorter end walls 40 assume a gentle arcuate configuration as depicted in FIGS. 6 and 7.

The base portion 32 exteriorally includes a plurality of mutually parallel and circumferentially extending grooves 42 which operably extend about the base and serve to facilitate grasping by an operating physician in a manner which will be discussed below.

The sidewall surfaces 38 of the hood portion includes a plurality of apertures 44 which are fashioned as elongate slots and extend through the hood portion of the general direction of a central longitudinal axis 46 of the microsurgical shield. The elongate slots 44 operably are dimensioned and positioned to be adjacent a cutting blade, a piercing and/or cutting blade 26 of a microsurgical scalpel, note again FIG. 1, and facilitate full re-sterilization during an autoclaving procedure by insuring full circulation around and about the microsurgical blade even though the blade is protected by the shield 24.

The bore 36 of the microsurgical shield 24 is interially fashioned with longitudinally extending slots 50 and 52. A base portion of the slots terminate in an abutting stop 54 and 56 respectively and each slot is fashioned with a raised land segment 60 and 62 as depicted in FIG. 4 the little f function. Function of the slots is to engage a compatibly dimensioned tab in a microsurgical scalpel as particularly depicted in FIG. 8–11.

Figure 8:
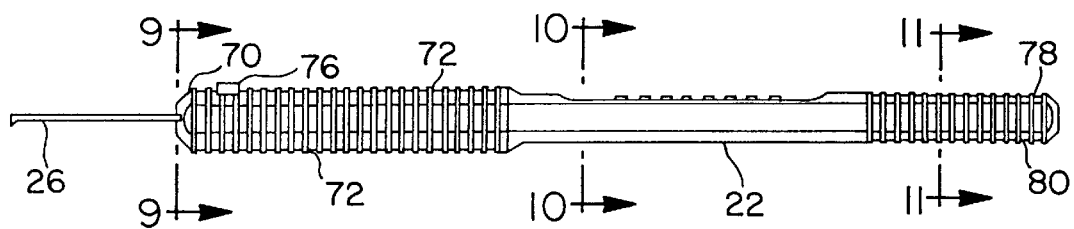
FIG. 8 is a side elevational view of a microsurgical scalpel in accordance with a preferred embodiment of the invention.
Figure 9:
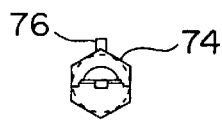
FIG. 9 is a cross-sectional view taken along section line 9—9 in FIG. 8.
Figure 10:
FIG. 10 is a cross-sectional view taken along section line 10—10 in FIG. 8.
Figure 11:
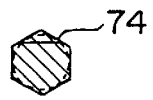
FIG. 11 is a cross-sectional view taken along section line 11—11 in FIG. 8.

Turning to those figures, FIG. 8 discloses a side elevational view of an elongate scalpel handle 22 as previously shown in FIG. 1. The handle 22, note particularly FIGS. 10 and 11 is a generally solid member having a hexagonal cross-sectional configuration. At one end 70 of the scalpel handle, an illustrative microsurgical blade 26 is releasably attached in a manner known to those of ordinary skill in the art and thus not presented in detail herein. The subject invention includes the provision of a combination of a plurality of circumferential and mutually parallel grooves 72 at the one end 70 of the scalpel which extend about the scalpel as depicted particularly in FIG. 8. An external hexagon configuration of the scalpel, note particularly FIG. 9, having side surfaces 74. This combination provides peripheral grooves 72 to permit the scalpel to be faciley manipulated in an axial direction by a surgeon while the hexagonal shape facilitates translational and rotational manipulation of the scalpel as desired during a surgical procedure. As shown in FIG. 9, an upstanding tab 76 or boss is integrally projected from the other end 70 of the scalpel handle and operably cooperates with and releasably engages one or the other of the elongate slots 50 and 52 as depicted in FIG. 4 during an assembly operation.

As shown in FIGS. 8 and 10, a mid portion of the scalpel 22 may be reduced by the creation of a land area 79 operable to receive indicia to identify the scalpel as desired.

A base end or other end 78 of the scalpel is also advantageously configured with a plurality of mutually parallel circumferential grooves or slots 80. It addition the base includes a hexagonal configuration having sides 74 which are extensions from the first end. The combination of circumferential grooves and hexagonal land surfaces enable the instrument to be faciley manipulated during surgery and for receiving the microsurgical shield in a manner to be discussed below.

Figure 12:
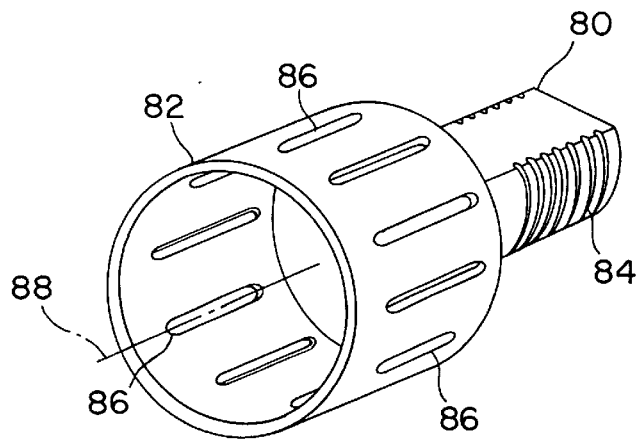
FIG. 12 is an axonometric view of a microsurgical scalpel shield in accordance with an alternate preferred embodiment of the invention.

FIG. 12 is an axonometric view of an alternate preferred embodiment of the invention wherein a microsurgical assembly includes a shield having a base 80 and an enlarged hood portion 82. The base 80 is fashioned with a plurality of mutually parallel, circumferential grooves or slots 84 to accommodate manipulation by a surgeon in a manner discussed in-connection with the embodiment depicted in FIG. 3. The internal structure base of the embodiment of the shield depicted in FIG. 12 is substantially identical to that depicted in FIGS. 4 and 5 and thus that disclosure is repeated by reference. new or different portion of the embodiment depicted in FIG. 12, as compared with the embodiment of the invention depicted in FIG. 3, comprises the hood portion 82 of the shield. In this connection, the hood 82 is fashioned as a cylindrical member having a radius greater than the lateral or offset dimension of a surgical instrument blade operable to utilize the shield. A plurality of elongate apertures 86 are fashioned through the cylindrical sidewalls of the hood 82 and generally are mutually parallel and extend in a direction parallel with an axis 88 of the shield as shown in FIG. 12. As discussed in connection with the embodiment of FIG. 3, the elongate slots or apertures 86 permit circulation during a re-sterilization and autoclaving procedure of the microsurgical scalpel.

Turning now to FIGS. 13–16, there will be seen yet another preferred embodiment of the invention wherein a microsurgical scalpel assembly 90 is depicted of a type operable or myringotomy procedures. A scalpel handle 92 carries an elongate surgical blade 94 of a type suitable for ear and throat surgery. Typically myringotomy blade lengths may be up to three inches and from 0 to 30 degrees of angulation with respect to a scalpel handle. The detail of the handle 92 is similar in all substantial respects with that depicted in FIGS. 8–11 and will not be repeated.

The microsurgical scalpel assembly 90 includes a shield structure 96 having a base portion 98 and a hood portion 100. The hood portion in the subject embodiment is fashioned in a general fan shape configuration to accommodate the elongate myringotomy surgical blade 94. The fan shaped configuration has in one embodiment a span of approximately 45 degrees, note FIG. 15. Generally flat opposing sidewall surfaces 102 as shown in FIGS. 13 and 16 are closed at the edges with arcuate side walls. The flat sidewall surfaces 102 are operably fashioned with a plurality of elongate apertures 104 which are designed to enhance autoclave re-sterilization of the blade 94 by permitting the free access and flow around the blade during an autoclaving procedure. A base portion 98 of the microsurgical shield includes an axial bore 106 in a manner previously discussed with respect to the embodiment of FIGS. 3–7 including at least one internal slot 108 which is operable to receive a corresponding tab, not shown, from a microsurgical scalpel 92 in a manner and position as previously illustrated in connection with FIG. 8. Accordingly in operation, the shield 96 is pushed over the base end of the scalpel 92 in the direction of arrow B toward the scalpel blade to cover the blade to snap into position and to operably cover the blade during a handling operation while concomitantly permitting full resterilization during an autoclaving procedure.

In each of the above embodiments of the invention, the hood is preferably fabricated from a clear polysulfone which is a high temperature polymer having structural rigidity and high temperature resistance to permit autoclave resterilization procedures.

While ophthalmology and otology scalpels have been depicted, the subject invention operable for use for other surgical grade scalpels where similar problems have been encountered.

Sequence of Utilization

Figure 17A:
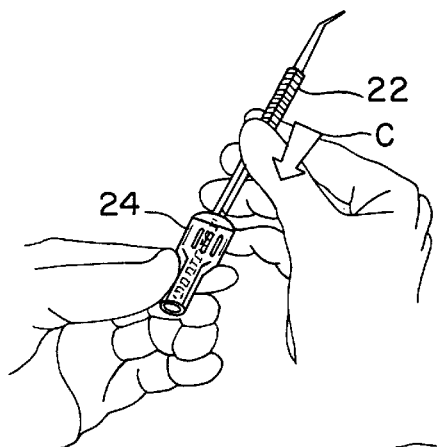
Figure 17B:
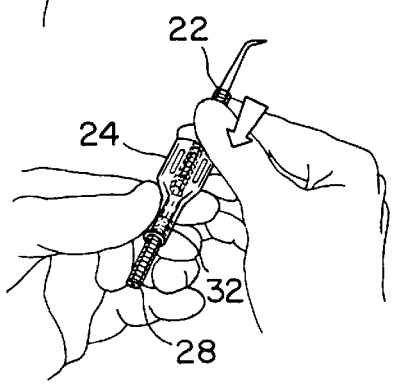
Figure 17C:
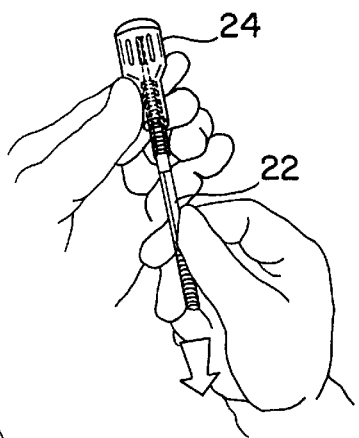

Referring specifically to FIGS. 17*a–c* there will be depicted a sequence of views showing a surgeons hands and a microsurgical shield to be applied to a microsurgical scalpel to form an assembly in accordance with the subject invention. More particularly, and as shown in FIG. 17*a*, a surgeon's left hand is shown holding a microsurgical shield 24 at its base by the circumferential grooves and the base end of the scalpel 22 is guided into the axial bore through the shield 24 as shown generally by directional arrow C. In FIGS. 17*b*, the surgeon is retaining his grasp on both instruments and a base 28 of the scalpel 22 projects through a base portion 32 of the microsurgical shield 24. Still further movement of the scalpel is effected by transferring the surgeons hand such that the right hand now grasps a mid portion of the scalpel handle and pulls a forward end of the scalpel into engagement wherein a tab 76 of the scalpel handle, note again FIG. 8, is slid into and engaged with a corresponding slot 50 or 52 within the shield 24, note particularly FIGS. 4 and 6.

In brief sequence, the scalpel is inserted into the shield with the knife blade pointing away from the surgeon and the base of the handle is guided into the large or expanded end of the microsurgical shield. In FIG. 17*b*, the handle is telescoped through the base or small portion of tho microsurgical shield. As depicted in FIG. 17*c*, holding the microsurgical protective shield firmly in the left hand, the right hand is transferred to the base of the scalpel and the scalpel handle is pulled through until it into a stop on the shield in a protective position around the blade.

Figure 18A:
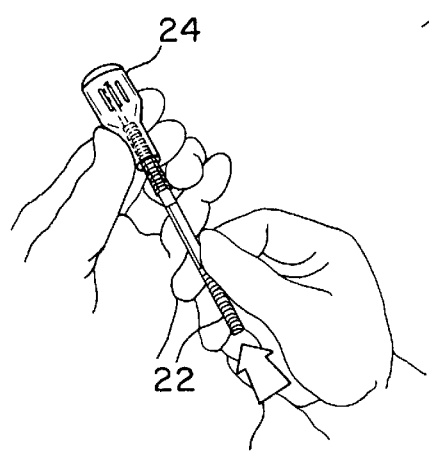
Figure 18C:
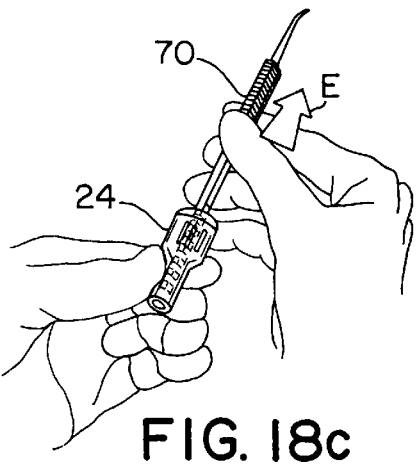
Figure 18B:
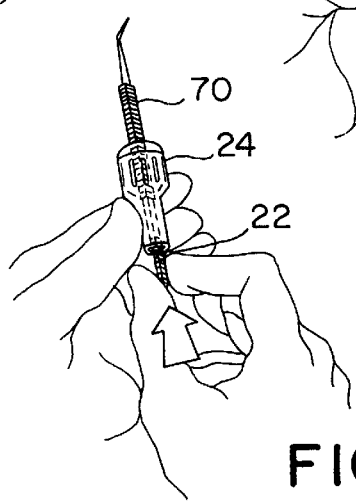

A reverse or removal sequence is depicted in FIGS. 18*a–c*. In this sequence, a surgeon operably grasps the base of the shield 24 with a left hand and pushes in the direction of arrow D the handle of the surgical scalpel, note particularly FIG. 18*a*. Further axial pushing is depicted in FIG. 18*b* until a forward end 70 of the scalpel 22 extends beyond the shield 24. At this time a surgeon may transfer his right hand to grasping the forward end 70 of the scalpel and remove the scalpel from the shield 24 in the direction of arrow E.

In sequence the removal process includes grasping the subject microsurgical scalpel assembly with the knife blade pointing away from the surgeon and firmly holding the microsurgical shield with the left hand while pushing the handle through the shield in the direction of the blade end as depicted in arrow D. Once enough handle is exposed as shown in FIG. 18*b*, a surgeon may transfer his right hand to a forward position on the handle as depicted in FIG. 18*c* and remove the surgical device without providing an opportunity for cutting or a puncture of any of the surgeon's fingers by a tip portion of the scalpel.

SUMMARY OF MAJOR ADVANTAGES OF THE INVENTION

After reading and understanding the foregoing description of various embodiments of the subject microsurgical scalpel assembly, in conjunction with the drawings, it will be appreciated that several distinct advantages of the subject invention are obtained. One major advantage is the provision of a microsurgical shield in cooperation with a scalpel to isolate a scalpel blade 26 from the hands of a surgeon during a handling operation. Assembly and disassembly of the subject invention is provided from a base end of the unit such that a surgeon is not required to guide or align a sharp surgical tip adjacent his own hands.

The enlarged microsurgical scalpel shield 24, 82 and 96, accommodate angulated offsets of conventional scalpel blades and a plurality of apertures permit full and complete re-sterilization of the blade during an autoclaving operation within a protective shield or hood.

The microsurgical scalpel handle is provided with a plurality of circumferential grooves near one end adjacent a scalpel blade and at an opposite end to facilitate handling, including assembly and disassembly of a microsurgical scalpel hood. An interior slot within the hood and a corresponding tab 76 upon the surgical handle permits the hood to be snap fit into position so that it may be faciley maintained during all handling operations.

The shields 24, 82 and 96 operably protect the point and cutting surfaces of high quality surgical instruments and thus a scalpel of fine grade and sharpness may be repetitively used and re-sterilized without becoming dull from inadvertent touching, bumping or laying against other surgical instruments which can take the fine edge off cutting surfaces.

In describing the invention, reference has been made to preferred embodiments and illustrative advantages of the invention. Those skilled in the art, however, after reading the subject disclosure, may recognize additions, deletions, modifications and/ or other changes which will fall within the purview of the subject invention and claims.

What is claimed:

1. A microsurgical scalpel assembly comprising:

an elongate scalpel handle;

a scalpel blade affixed at one end of said scalpel handle and extending away from said scalpel handle, said scalpel blade terminating with at least one operative cutting edge; and a shield releasably connected to said one end of said scalpel handle and extending away from said one end of said scalpel handle to operably surround said scalpel blade, said shield having a base portion operable to releasably engage said one end of said scalpel handle; and a hood portion connected to said base portion, said hood portion having an enlarged cross-sectional configuration with respect to said base portion and being radially spaced from and operably surrounding said scalpel blade, said hood portion being essentially rectangular at any cross-section taken along a line normal to a central longitudinal axis of said elongate scalpel handle and the area of each sequential cross-section increasing at each location further away from said base portion such that said hood portion exhibits a fanned out configuration to accommodate an extended and angulated configuration of said scalpel blade with respect to said elongate scalpel handle;

said hood being fashioned with a plurality of apertures to operably facilitate sterilization of said scalpel blade of said microsurgical scalpel assembly;

wherein the shield operably isolates the scalpel blade from a surgeon's hands during handling and from becoming damaged through contacting other instruments or surfaces during a sterilization procedure yet may be facilely removed by a surgeon to utilize the microsurgical scalpel during a surgical procedure.

2. A microsurgical scalpel assembly comprising an elongated handle having a blade end, a base end, an axis extending longitudinally therethrough, and a grasping surface surrounding said axis, said handle being provided with a radially projecting tab adjacent to said blade end;

a blade extending from said blade end of said handle and having a distal blade tip angled with respect to said axis and extending radially beyond said grasping surface of said handle;

a scalpel shield adapted to be fitted to said scalpel handle and to extend axially beyond said blade end of said handle and beyond said distal blade tip, said protective shield comprising:

a base having a cylindrical bore extending therethrough, said bore having a diameter adapted to said handle, whereby said base of said shield is slidably and rotatably supported on said handle, said bore being provided with elongate slots capable of engaging said projecting tab of said handle to prevent said hood from rotating about said axis of said handle; and a hood integral with said base and extending axially therefrom to surround said blade and capable of extending beyond said distal tip of said blade, said hood having a pair of mutually opposing long sidewall surfaces and a pair of mutually opposing short sidewall surfaces, said sidewalls being joined to form a structure having a generally rectangular cross section in a plane perpendicular to said axis of said handle and capable of surrounding said blade, said long sidewalls being spaced apart a distance essentially equivalent to said diameter of said bore, whereby said projecting tab of said handle is prevented from entering said hood unless said scalpel is rotatably positioned with said projecting tab directed generally toward one of said short sidewalls.

* * * * *